(12) United States Patent
Swisher

(10) Patent No.: US 8,221,388 B2
(45) Date of Patent: Jul. 17, 2012

(54) BIASED CLAMPING ASSEMBLIES

(75) Inventor: David R. Swisher, St. Charles, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 244 days.

(21) Appl. No.: 12/757,148

(22) Filed: Apr. 9, 2010

(65) Prior Publication Data

US 2010/0274174 A1 Oct. 28, 2010

Related U.S. Application Data

(60) Provisional application No. 61/171,659, filed on Apr. 22, 2009.

(51) Int. Cl.
*A61M 25/00* (2006.01)
(52) U.S. Cl. ........................................ 604/530
(58) Field of Classification Search .............. 604/530
See application file for complete search history.

(56) References Cited

U.S. PATENT DOCUMENTS

| | | |
|---|---|---|
| 1,330,523 A | 2/1920 | Evitts et al. |
| 1,959,074 A | 5/1934 | Bloxsom |
| 2,595,511 A | 5/1952 | Butler |
| 2,844,351 A | 7/1958 | Smith |
| 3,429,549 A | 2/1969 | Swanson |
| 4,248,401 A | 2/1981 | Mittleman |
| 4,292,969 A | 10/1981 | Raible et al. |
| 4,306,705 A | 12/1981 | Svensson |
| 4,307,869 A | 12/1981 | Mittleman |
| 4,434,963 A | 3/1984 | Russell |
| 4,439,179 A | 3/1984 | Lueders et al. |
| 4,560,378 A | 12/1985 | Weiland |
| 4,570,898 A | 2/1986 | Staeubli |
| 4,586,691 A | 5/1986 | Kozlow |
| 4,932,629 A | 6/1990 | Rodomista et al. |
| 4,950,255 A | 8/1990 | Brown et al. |
| 5,035,399 A | 7/1991 | Rantanen-Lee |
| 5,071,411 A | 12/1991 | Hillstead |
| 5,158,553 A | 10/1992 | Berry et al. |
| 5,257,770 A | 11/1993 | Grove |
| 5,318,546 A | 6/1994 | Bierman |

(Continued)

FOREIGN PATENT DOCUMENTS

DE 94 08 633 U1 10/1994

(Continued)

OTHER PUBLICATIONS

European Search Report dated Mar. 29, 2010 in copending European Patent Appln. No. 09180739.0.

(Continued)

*Primary Examiner* — Matthew F Desanto
*Assistant Examiner* — Jason Flick
(74) *Attorney, Agent, or Firm* — Thomas M. Johnston, Esq.

(57) ABSTRACT

A medical clamping assembly includes a housing defining a chamber and a deflecting member operable to slide relative to the housing between a first position and a second position. A conduit is also provided within the housing and is adapted for fluid coupling to a medical device. The medical clamping assembly also includes a biasing element disposed within the housing adjacent to the conduit. The deflecting member is movable relative to the housing between the first position corresponding to an open state of the conduit and the second position corresponding to a closed state of the conduit whereby the biasing element compresses the conduit to substantially close a lumen of the conduit.

18 Claims, 8 Drawing Sheets

U.S. PATENT DOCUMENTS

| | | | |
|---|---|---|---|
| 5,352,214 | A | 10/1994 | Oscarsson |
| 5,423,769 | A | 6/1995 | Jonkman et al. |
| 5,489,274 | A | 2/1996 | Chu et al. |
| 5,853,398 | A | 12/1998 | Lal et al. |
| 6,217,564 | B1 * | 4/2001 | Peters et al. ............. 604/523 |
| 6,592,558 | B2 | 7/2003 | Quah |
| 6,610,027 | B1 | 8/2003 | El Hatu |
| 6,689,109 | B2 | 2/2004 | Lynn |
| 6,742,760 | B2 | 6/2004 | Blickhan et al. |
| 7,011,645 | B2 * | 3/2006 | McGuckin et al. ......... 604/34 |
| 7,018,374 | B2 | 3/2006 | Schon et al. |
| 7,094,218 | B2 | 8/2006 | Rome et al. |
| 7,182,746 | B2 | 2/2007 | Haarala et al. |
| 7,306,586 | B2 | 12/2007 | Beaufore et al. |
| 7,311,697 | B2 | 12/2007 | Osborne |
| 7,364,571 | B2 | 4/2008 | Schinazi et al. |
| 7,381,204 | B2 | 6/2008 | Wilson et al. |
| 7,947,019 | B2 * | 5/2011 | Perchik et al. ............ 604/175 |
| 2002/0062106 | A1 | 5/2002 | Chu et al. |
| 2003/0040724 | A1 | 2/2003 | Lynn |
| 2003/0225379 | A1 | 12/2003 | Schaffer et al. |
| 2004/0064086 | A1 | 4/2004 | Gottlieb et al. |
| 2004/0171997 | A1 | 9/2004 | Wilson et al. |
| 2004/0186445 | A1 | 9/2004 | Raulerson et al. |
| 2004/0249349 | A1 | 12/2004 | Wentling |
| 2005/0256447 | A1 | 11/2005 | Richardson et al. |
| 2006/0015074 | A1 | 1/2006 | Lynn |
| 2006/0058738 | A1 * | 3/2006 | Ponzi et al. ............... 604/180 |
| 2006/0081797 | A1 | 4/2006 | Zerfas |
| 2006/0149214 | A1 | 7/2006 | Breiter et al. |
| 2006/0189922 | A1 | 8/2006 | Amarasinghe et al. |
| 2007/0112313 | A1 | 5/2007 | Fangrow |
| 2007/0225682 | A1 | 9/2007 | Ash et al. |
| 2007/0255229 | A1 | 11/2007 | Kane et al. |
| 2008/0021415 | A1 | 1/2008 | Durkin et al. |
| 2008/0029721 | A1 | 2/2008 | Miyahara |
| 2008/0051731 | A1 | 2/2008 | Schweikert et al. |
| 2008/0082080 | A1 | 4/2008 | Braga |
| 2009/0005759 | A1 * | 1/2009 | Chelak .................... 604/533 |
| 2009/0030378 | A1 | 1/2009 | Garcia |
| 2010/0108058 | A1 * | 5/2010 | Glusker et al. ......... 128/200.14 |

FOREIGN PATENT DOCUMENTS

| | | |
|---|---|---|
| EP | 1360973 A1 | 11/2003 |
| WO | WO 97/11296 | 3/1997 |

OTHER PUBLICATIONS

International Search Report, Application No. PCT/US2010/030978 dated Jun. 16, 2010.

* cited by examiner

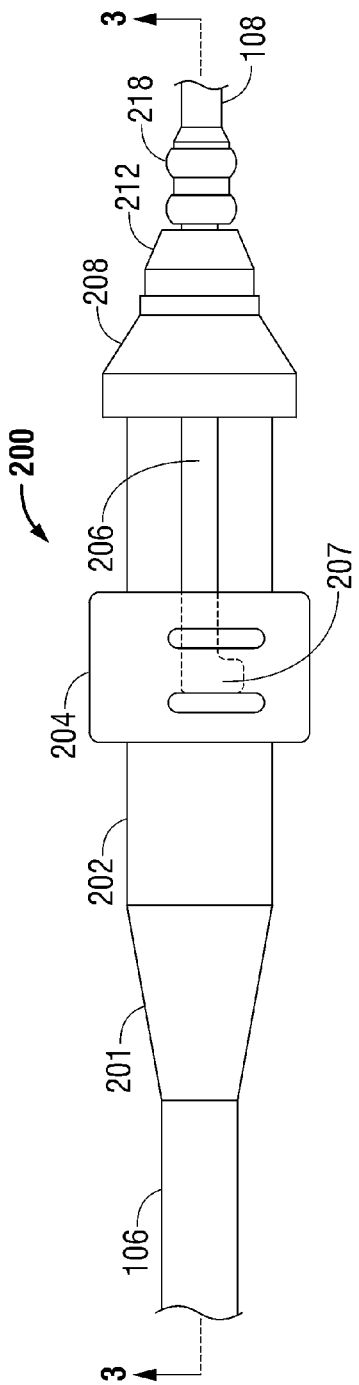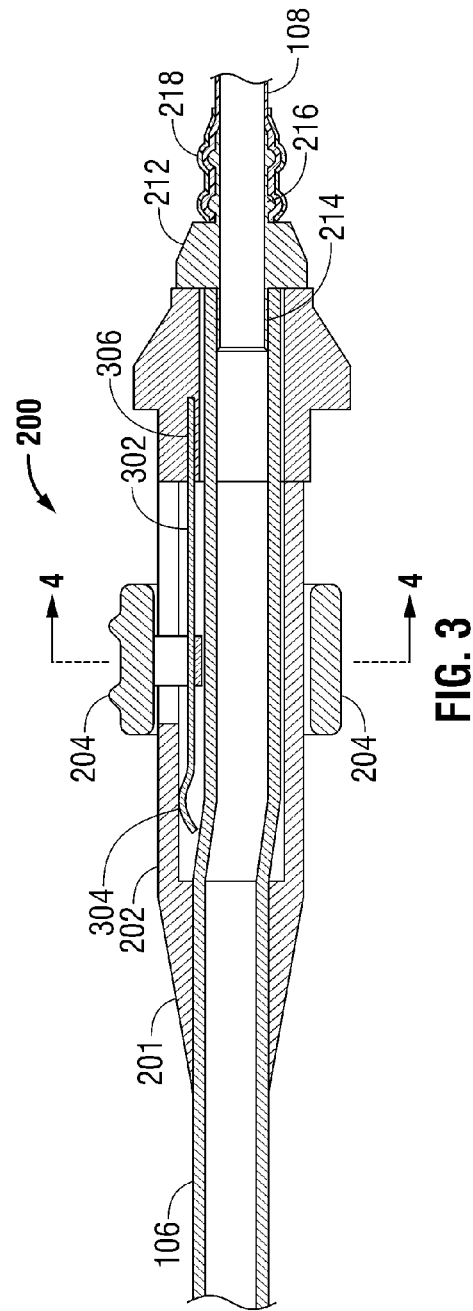
FIG. 2
FIG. 3

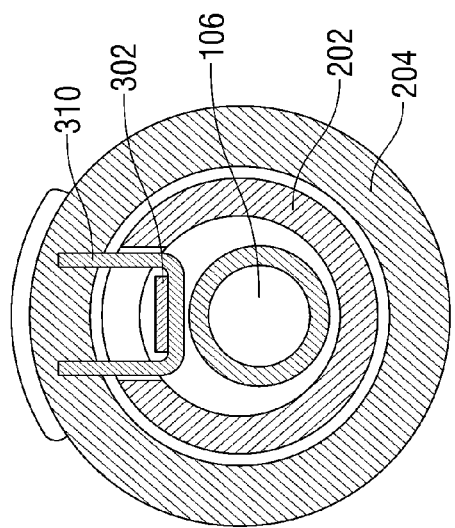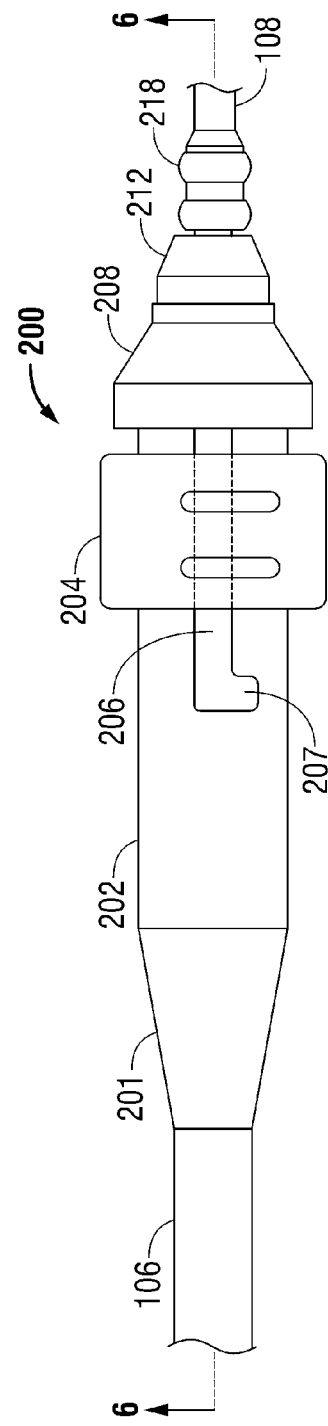

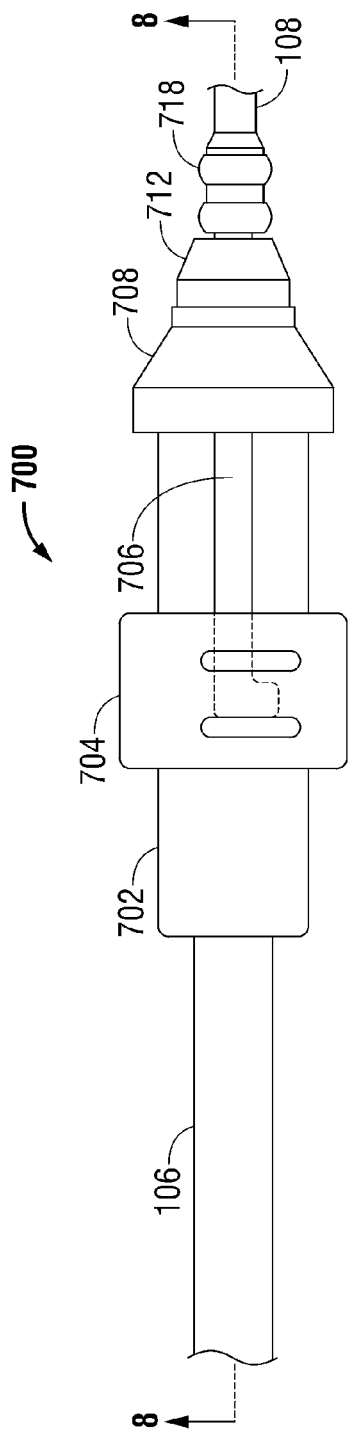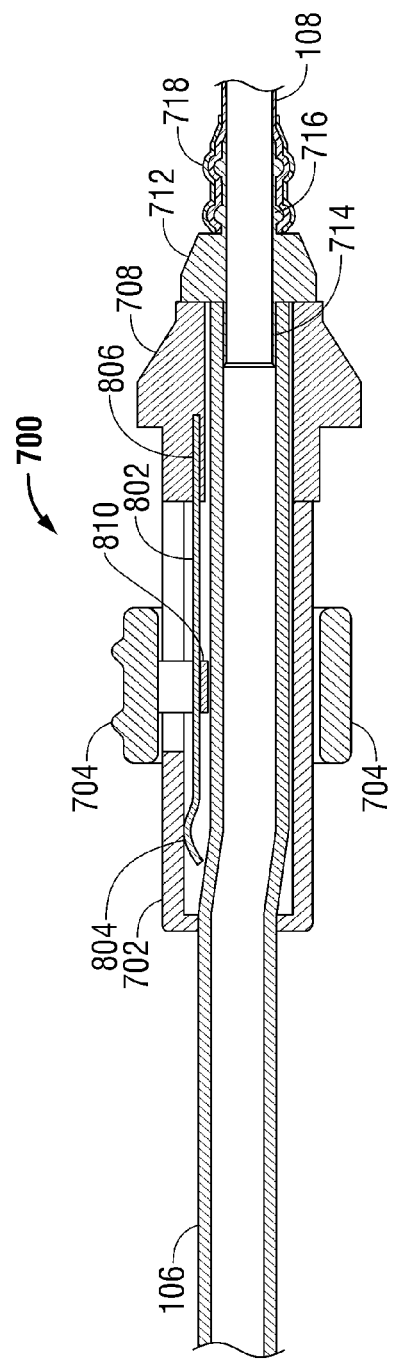

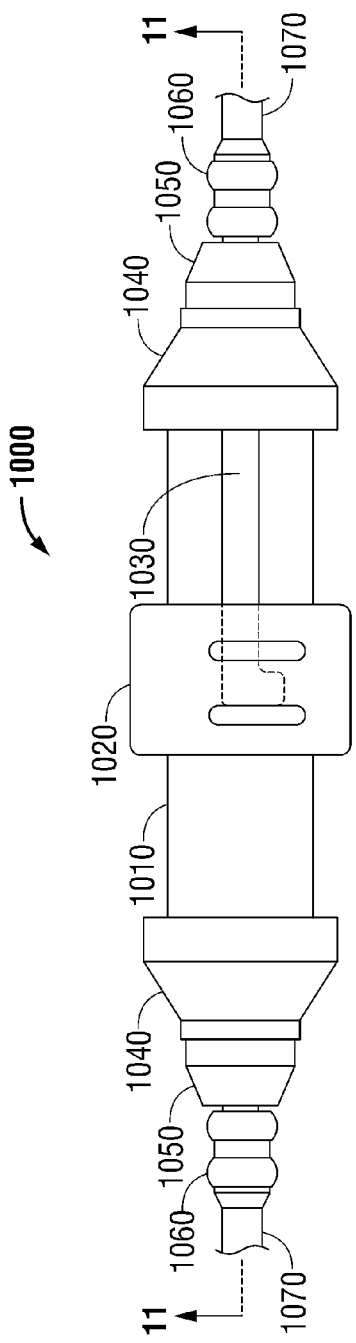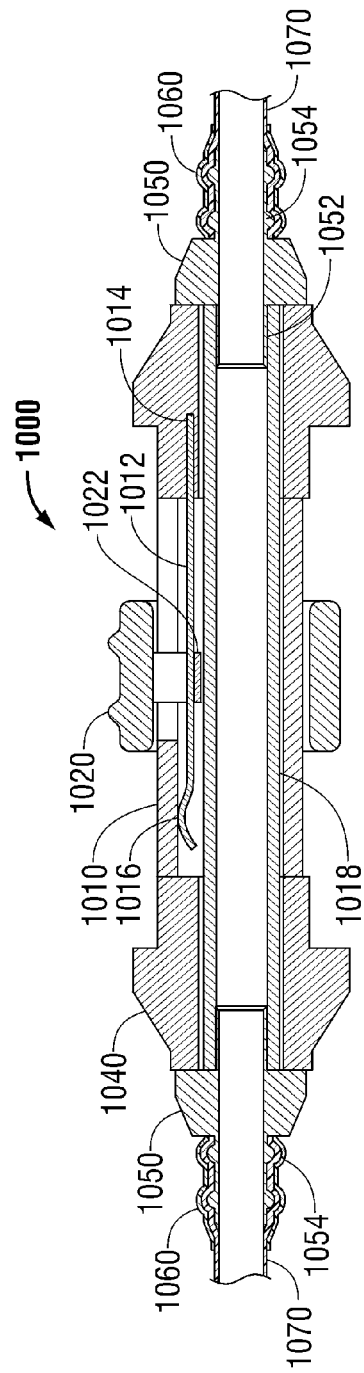

BIASED CLAMPING ASSEMBLIES

CROSS REFERENCE TO RELATED APPLICATIONS

The present application claims priority to U.S. Provisional Application Ser. No. 61/171,659, filed Apr. 22, 2009, entitled "BIASED CLAMPING ASSEMBLIES", the contents of which are hereby incorporated by reference in their entirety.

BACKGROUND

1. Technical Field

The present disclosure relates generally to clamping assemblies for flexible fluid conduits, and, in particular, to a clamping assembly for obstructing fluid flow through extension conduits of catheter assemblies.

2. Description of the Related Art

Catheters are flexible medical devices which facilitate the withdrawal and introduction of fluids from and to body cavities, ducts, and vessels. Catheter assemblies may have particular application in a hemodialysis procedure where blood is withdrawn from a blood vessel for treatment, and subsequently returned to the blood vessel for circulation. Known hemodialysis catheters include multiple lumens, such as dual lumen or triple-lumen catheters, which permit bi-directional fluid flow within the catheter whereby one lumen is dedicated for withdrawal of blood from a body vessel and the other lumen is dedicated for returning the treated blood to the vessel. During an exemplary hemodialysis procedure, a multiple lumen catheter is inserted into a body and blood is withdrawn through an arterial lumen of the catheter. The removed blood is directed to a hemodialysis unit which dialyzes, or purifies, the blood to remove waste and toxins from the blood. The dialyzed blood is returned to the patient through a venous lumen of the catheter.

Various techniques and apparatus are employed for the insertion of hemodialysis catheters including, e.g., guidewires, introduction stylets or the like. Some of these known techniques include subcutaneous tunneling methodologies where a subcutaneous tunnel is formed between two spaced openings in the skin with the use of a trocar or the like. One catheter end is introduced through an entry site or venotomy site for routing into, e.g., the jugular vein and routed to the heart. The trailing or proximal end is advanced through the subcutaneous tissue to exit a second exit opening adjacent the sternum of the patient beneath the venotomy site. Once the proximal end of the catheter is exposed, a catheter hub with extension conduits is fluidly connected to the catheter. One subcutaneous technique is disclosed in U.S. Pat. No. 5,509,897 to Twardowski et al., the contents of which are incorporated herein by reference in its entirety.

SUMMARY

The present disclosure relates to a medical clamping assembly for use with a catheter including a housing that defines a chamber. The assembly includes a deflecting member that slides relative to the housing between a first position of the housing and a second position of the housing. The clamping assembly also includes a conduit within the housing adapted for fluid coupling to the catheter and a biasing element disposed within the housing adjacent to the conduit. The deflecting member moves between the first position of the housing corresponding to an open state of the conduit and the second position of the housing corresponding to a closed state where the biasing element compresses the conduit to substantially close a lumen of the conduit. The housing further includes a track having a notch at the first position of the housing. The deflecting member slides in the track and is held in place at the first position of the housing by the notch. The biasing element is a metal spring member that is formed from stainless steel having a grade 301, 302, or 304 or a shape memory alloy such as nitinol. The clamping assembly also includes a cradle coupled to the deflecting member. The biasing element rests on the cradle so that when the deflecting member is at the first position of the housing, the cradle prevents the biasing element from compressing the conduit. The biasing element is in a normally closed state and biases the deflecting member toward the second position of the housing. The medical clamping assembly has an adaptor at a distal end of the housing that is operatively connected to the catheter and includes a luer connector. The medical clamping assembly has another adaptor with a luer connector at a proximal end of the housing that secures the biasing element in the housing and is operatively connected to an extension conduit fluidly coupled to a dialysis unit.

The present disclosure also relates to a medical clamping assembly for use with a catheter including a housing that defines a chamber. The assembly includes a deflecting member that slides relative to the housing between a first position of the housing and a second position of the housing. The clamping assembly also includes a biasing element disposed within the housing adjacent to the conduit. The deflecting member moves between the first position of the housing corresponding to an open state and the second position of the housing corresponding to a closed state where the biasing element compresses a conduit extending through the medical clamping assembly to substantially close a lumen of the conduit. A first end of the conduit is fluidly coupled to the catheter and a second end of the conduit is fluidly coupled to a dialysis unit and the medical clamping assembly is movable relative to the conduit.

The present disclosure also relates to a catheter assembly. The catheter assembly includes a catheter, a dialysis conduit, and a clamping assembly operatively connected in between the catheter and the dialysis conduit. The clamping assembly has a housing defining a chamber, a deflecting member operable to slide along the housing between a first position and a second position, a conduit extending through the housing and being adapted for fluid coupling to the catheter and the dialysis unit, and a biasing element disposed within the housing adjacent to the conduit. The deflecting member being movable relative to the housing between the first position corresponding to an open state of the conduit and the second position corresponding to a closed position of the conduit whereby the biasing element compresses the conduit to substantially close a lumen of the conduit.

BRIEF DESCRIPTION OF THE DRAWINGS

Various embodiments of the presently disclosed catheter clamping system are described herein with references to the accompanying drawings, wherein:

FIG. 2 is a side view of a catheter assembly with a clamping assembly in an open condition according to an embodiment of the present disclosure;

FIG. 3 is a cross-sectional view of the catheter assembly shown in FIG. 2 taken along the lines 3-3;

FIG. 4 is a cross-sectional view of the catheter assembly shown in FIG. 3 taken along the line 4-4;

FIG. 5 is a side view of the catheter assembly with a clamping assembly in a closed condition according to an embodiment of the present disclosure;

FIG. 7 is a side view of a catheter assembly with a clamping assembly according to another embodiment of the present disclosure;

FIG. 8 is a cross-sectional view of the catheter assembly shown in FIG. 7 taken along the lines 8-8;

FIG. 10 is a side view of a catheter assembly with a clamping assembly according to another embodiment of the present disclosure;

FIG. 11 is a cross-sectional view of the catheter assembly shown in FIG. 10 taken along the lines 11-11;

DETAILED DESCRIPTION OF THE EMBODIMENTS

Figure 1:
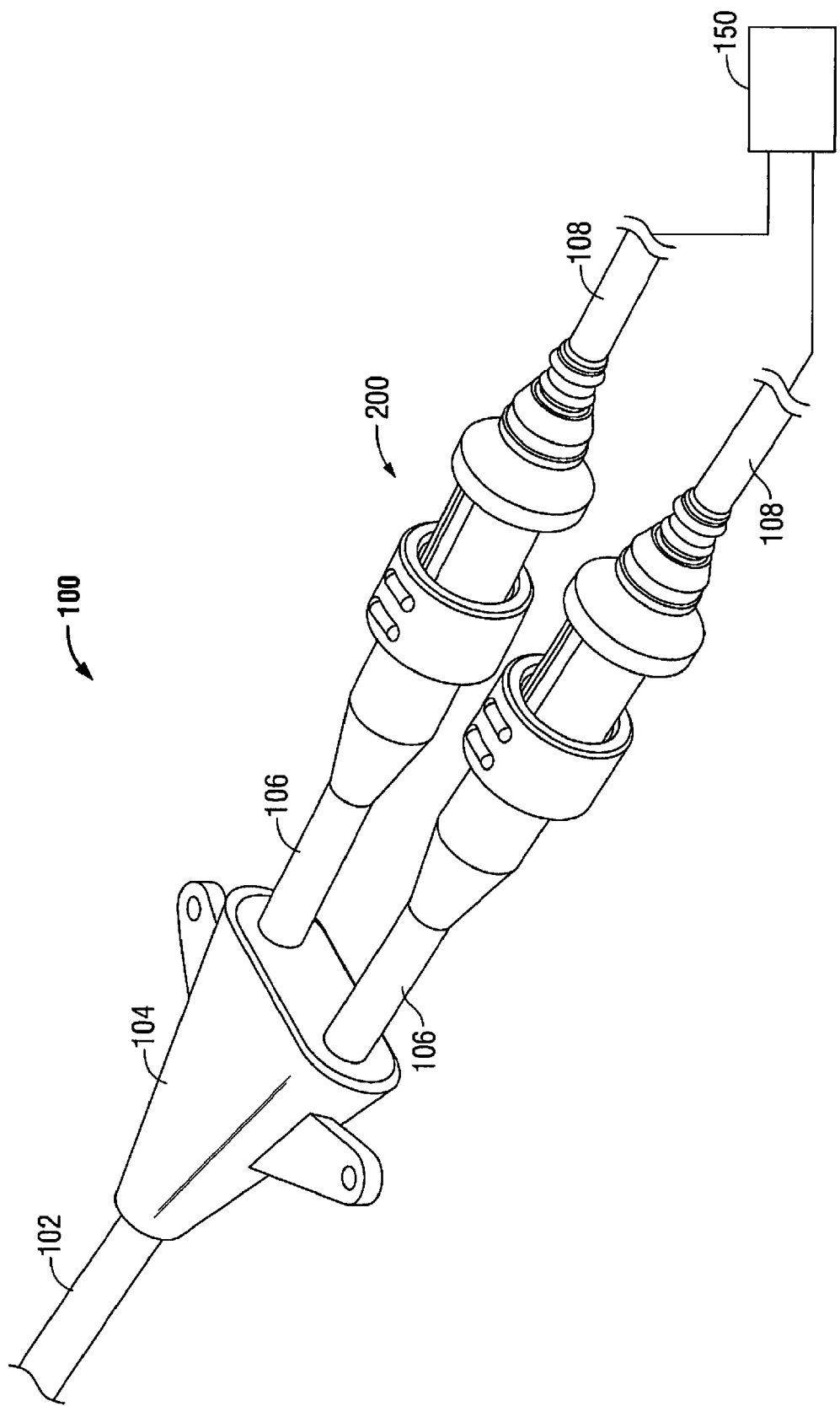
FIG. 1 is a perspective view of a catheter assembly with a clamping assembly according to an embodiment of the present disclosure.

Hereinafter, embodiments of the presently disclosed catheter assemblies will be described with reference to the accompanying drawings. Like reference numerals refer to similar or identical elements throughout the description of the figures. In the discussion that follows, the term "proximal" or "trailing" will refer to the portion of a structure that is closer to a clinician or dialysis system, while the term "distal" or "leading" will refer to the portion of the structure that is farther from the clinician or dialysis system. As used herein, the term "subject" refers to a human patient or other animal. The term "clinician" refers to a doctor, nurse or other care provider and may include support personnel.

The presently disclosed catheter clamping assemblies is employed with dialysis systems, but is also suitable for other devices that use clamping assemblies to open and close conduits or tubes. A catheter assembly according to an embodiment of the present disclosure, such as catheter assembly 100 shown in FIG. 1, includes a catheter 102, a hub or housing 104 and extension conduits 106. The hub 104 fluidly interconnects catheter 102 and extension conduits 106. Extension conduits 106 are formed from standard silicone tubes. Catheter assembly 100 additionally includes a pair of clamping assemblies 200 operatively associated with each extension conduit 106. Each clamping assembly 200 is configured to compress an extension conduit 106, thereby obstructing or at least hindering fluid flow through the extension conduit 106. In this embodiment, adjacent to the proximal end of each clamping assembly 200 is a proximal extension or dialysis conduit 108 that is connected directly or indirectly to a dialysis system 150 (as shown schematically in FIG. 1).

Referring to FIG. 2, a clamping assembly shown generally as 200, has a housing 202 having a distal portion 201 and a proximal portion 208 that fit over extension conduit 106 and position the clamping assembly 200 about the extension conduit 106. In one embodiment, clamping assembly 200 slides and rotates relative to extension conduit 106 or is secured to extension conduit 106 to prevent relative movement, such as through the use of adhesives, solvent bonding, sonic welding or a press fit between at least one end portion of the housing 202 and the extension conduit 106. The extension conduit 106 extends from the distal end of the clamping assembly 200 through the distal portion 201 and a chamber defined by housing 202. Distal portion 201 positions the extension conduit 106 in place and helps prevent the extension conduit 106 from kinking when it enters the chamber defined by housing 202. Housing 202 has an "L" shaped track 206 in which a deflecting member or sliding tab 204 can slide from a first position near the distal end to a second position near the proximal end of housing 202 along track 206. Although FIG. 2 depicts an "L" shaped track in this embodiment, any shaped track having at least one notch or protrusion at either the distal or proximal end (such as "T" or "I" shaped tracks) may be used. Sliding tab 204 defines the valve open or close configuration and drives an internal biasing element that will be discussed hereinbelow. When sliding tab 204 slides to the distal end of track 206 toward notch 207, sliding tab 204 can be rotated in a clockwise or counterclockwise direction around the housing 202 to lock the sliding tab 204 in place. As shown in FIG. 2, the notch 207 is located downward which would require the clinician to rotate the sliding tab 204 downward in the direction of the notch 207 to lock the sliding tab 204 in place. Although not shown, the notch could be located in the upward direction which would require the clinician to rotate the sliding tab 204 upward in the direction of the notch to lock the sliding tab 204 in place. In this embodiment, sliding tab 204 is urged towards proximal portion or leer adaptor 208 of housing 202 (by biasing element 302 as shown in FIG. 3) to bias sliding tab 204 in the proximal direction, towards the closed configuration unless locked in place in notch 207. Alternatively, sliding tab 204 may be urged in the distal direction towards the open position.

In this embodiment, proximal to clamping assembly 200 is an adaptor 212, which will be described in more detail below with regard to FIG. 3, which receives extension conduits 106 and 108. Adaptor 212 fluidly interconnects extension conduit 106 to extension conduit 108. A shrink sleeve 218 is provided to seal the extension conduit 108 to adaptor 212 to prevent leakage of fluid as shown in FIG. 3.

Housing 202 can be labeled or multicolored to indicate a state of the clamp. For instance, proximal end 208 of housing 202 (as shown by the letter "O" in FIG. 2) could be labeled with the word "open", have a symbol that represents an open state or be colored green to indicate that the clamping assembly 200 is in an open state. The area surrounding notch 207 (as shown by the letter "C" in FIG. 5, could be labeled with the word "closed", have a symbol that represents a closed state or be colored red to indicate that the clamping assembly 200 is in closed state. Alternatively, a variety of colors and/or indicia may be used to identify the state of the clamp. As such, when the clamp is in an open state as shown in FIG. 2, the clinician can easily visualize that the clamp is in an open state. If the clamp is in a closed state as will be described below with regard to FIG. 5, the clinician can easily visualize that the clamp is in a closed state.

FIG. 3 depicts a cross section of the clamping assembly 200 shown in FIG. 2 taken along the lines 3-3. As shown in FIG. 3, clamping assembly 200 has a biasing element 302 that can be deflected without yielding. Biasing element is a metal spring member 302 made from a stainless steel, e.g., a stainless steel having a grade 301, 302, or 304 or a shape memory alloy such as Nitinol. Nitinol is derived from its place of discovery (Nickel Titanium Naval Ordnance Laboratory) and is nickel titanium. The distal end 304 of metal spring member 302 is curved and rests against an inner wall of housing 202. Due to the curvature of the metal spring member 302 at distal end 304, the metal spring member 302 slides smoothly along the inner wall of housing 202. The proximal end 306 of metal spring member 302 is bonded or molded in place in proximal portion 208 of housing 202 to secure the metal spring member 302 to the clamping assembly 200. Metal spring member 302 is biased to a normally closed position which would pinch or clamp the extension conduit 106. Metal spring member 302 extends through a cradle 310 connected to slide tab 204 as shown in FIG. 4.

Adaptor 212 has an annular projection 214 that extends into extension conduit 106. In this embodiment, annular projection 214 is press fitted into extension conduit 106 or solvent bonded to provide a leak proof seal. Adaptor 212 also has an annular projection 216 that is fluidly connected to extension conduit 108. As shown in FIG. 3, extension conduit fits over annular projection 216. A shrink sleeve 218 is also provided to seal extension conduit 108 to annular projection 216 to provide a leak proof seal. Adaptor 212 is sonic welded or solvent bonded to proximal portion 208 of housing 202.

FIG. 4 depicts a cross section of the clamping assembly shown in FIG. 3 taken along the lines 4-4. As shown in FIG. 4, extension conduit 106 runs through the center of housing 202. Cradle 310 is connected to the slide tab 204 with metal spring member 302 resting on the cradle 310.

Figure 6:
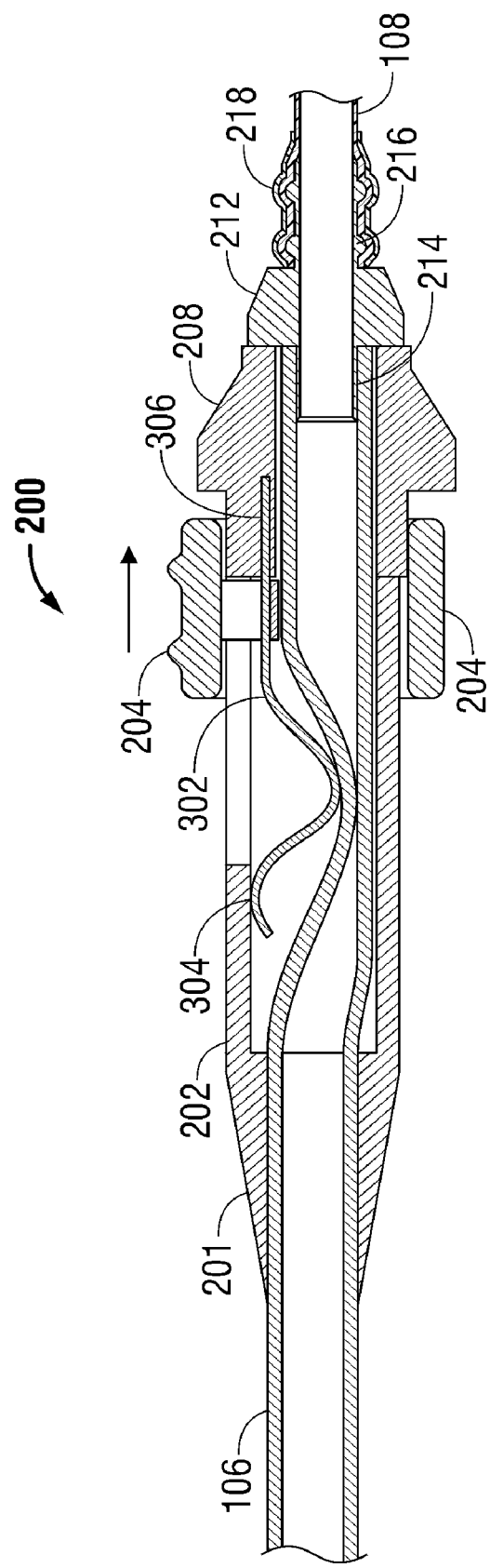
FIG. 6 is a cross-sectional view of the catheter assembly shown in FIG. 5 taken along the lines 6-6.

FIGS. 5 and 6 depict the clamping assembly 200 in a closed state. As shown in FIG. 5, the slide tab 204 is moved to the proximal end of housing 202. FIG. 6 shows a cross section of the clamping assembly 200 of FIG. 5 taken along the lines 6-6. In clamping assembly 200, metal spring member 302 is in its normally closed position which pinches or clamps the extension conduit 106 at portion 602 thereby obstructing the flow of fluid through the conduit 106.

During operation of the clamping assembly 200, when the slide tab 204 is near the proximal end of the housing 202, the metal spring member 302 is in its normal position and pinches the extension conduit 106 at portion 602 as shown in FIG. 6. When the slide tab 204 is placed in the distal position, the cradle 310 straightens the normally curved or closed metal spring member 302 thereby placing the clamp in an open state as shown in FIG. 3.

FIG. 7 depicts another embodiment of a clamping assembly 700. Similar to clamping assembly 200 of FIG. 2, clamping assembly 700 has a housing 702 with a slide tab 704 that runs along a track 706. At the proximal end of housing 702 is a male luer adaptor 708 formed integral to housing 702 that receives a corresponding female luer adaptor 712 of a dialysis conduit from a dialysis system to provide a seal between extension conduit 106 and the dialysis conduit.

FIG. 8 is a cross section of the clamping assembly shown in FIG. 7 taken along the lines 8-8. As shown in FIG. 8, clamping assembly 700 has a metal spring member 802 that can be deflected without yielding. The distal end 804 of metal spring member 802 is curved and rests against an inner wall of housing 702. The proximal end 806 of metal spring member 802 is bonded or molded in place in male luer adaptor 708 to secure the metal spring member 802 to the clamping assembly 700 in one embodiment. Metal spring member 802 is biased to a normally closed position which would clamp the extension conduit 106. Metal spring member 802 extends through a cradle 810 connected to slide tab 704. The distal end of housing 702 terminates at the end of a chamber defined by housing 702 and is positioned over the extension conduit 106 snugly to secure the extension conduit inside the housing 702. Extension conduit 106 may be bonded to the distal end of housing 702 to prevent relative movement between the extension conduit 106 and housing 702, such as through the use of adhesives, solvent bonding, sonic welding or a press fit between at least one end portion of the housing 702 and the extension conduit 106. Unlike clamping assembly 200 of FIGS. 2 and 3, housing 702 does not have a distal portion 201 to position the extension conduit 106 in place. Female luer adaptor 712 is similar to adaptor 212 and has an annular projection 714 and annular projection 716. Shrink sleeve 718 is also provided to provide a leak proof seal.

Figure 9:
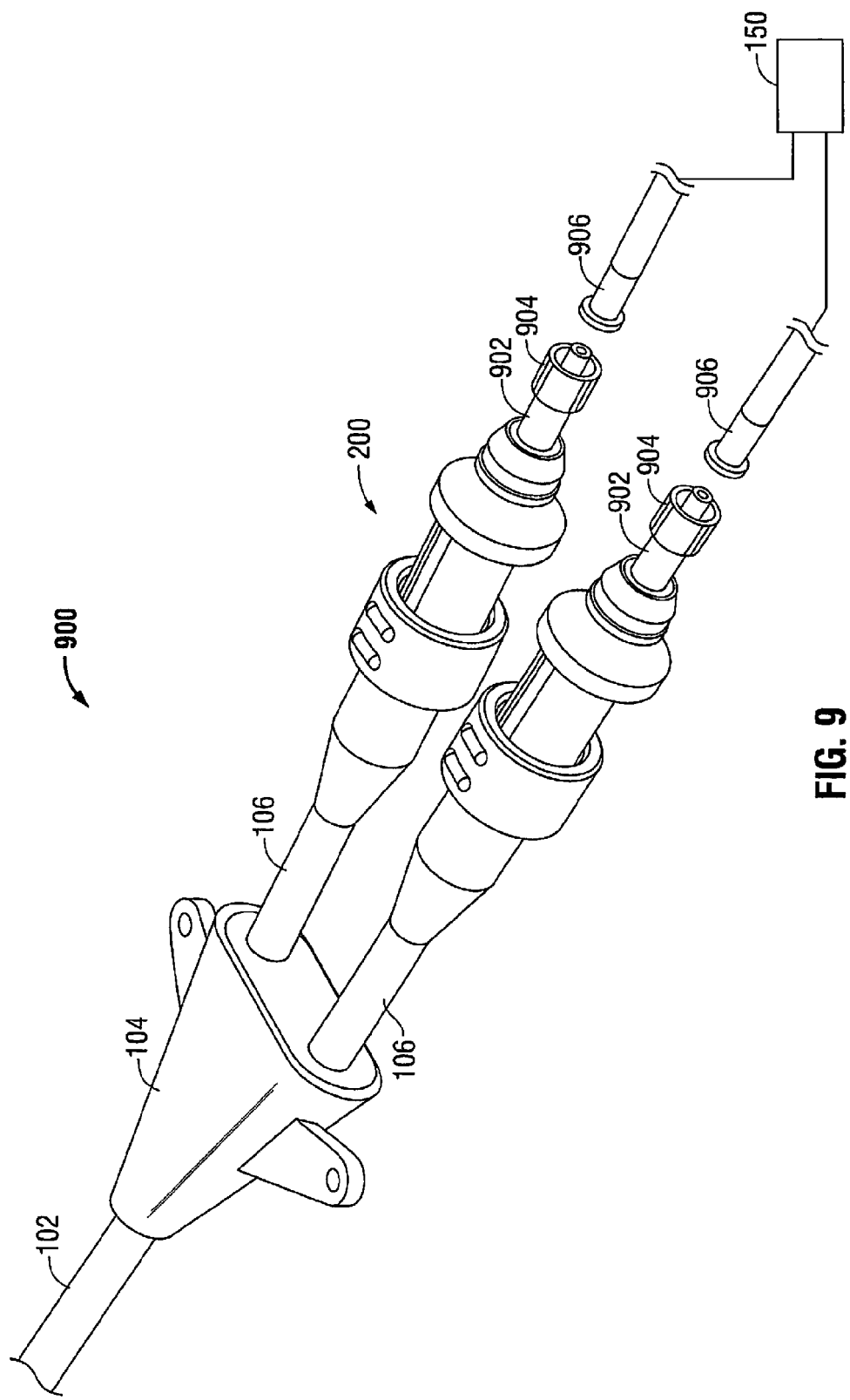
FIG. 9 is a perspective view of a catheter assembly with a clamping assembly according to another embodiment of the present disclosure.

FIG. 9 depicts another embodiment of a catheter assembly 900. Catheter assembly 900 includes a catheter 102, a hub 104 and extension conduits 106. Catheter assembly 900 additionally includes a pair of clamping assemblies 200 operatively associated with each extension conduit 106. Attached to the proximal end of each clamping assembly 200 is an extension conduit 902 that is terminated by a luer connector 904. Luer connector 904 allows a clinician to easily connect and disconnect extension conduit 902 from conduit 906 which leads directly or indirectly to a dialysis system 150 (as shown schematically in FIG. 9).

FIG. 10 depicts a clamping assembly 1000 in accordance with another embodiment of the present disclosure. Clamping assembly 1000 is similar to clamping assembly 200 in that clamping assembly 1000 has a housing 1010, a deflecting member or slide tab 1020 and a track 1030. The proximal and distal ends of clamping assembly 1000 each have a male luer adaptor 1040 that is fluidly connected to a female luer adaptor 1050.

FIG. 11 depicts a cross section of the clamping assembly 1000 of FIG. 10 taken along the lines 11-11. As can be seen in FIG. 11, the clamping assembly 1000 has a conduit 1018 extending from the proximal end to the distal end of the clamping assembly 1000. Adjacent to conduit 1018 is biasing element or metal spring member 1012 having a distal curved end 1016. Proximal end 1014 of biasing element 1012 is bonded or formed in male luer adaptor 1040. Biasing element 1012 rests in cradle 1022 which is attached to slide tab 1020. Each female luer adaptor 1050 is similar to adaptor 212 and has an annular projection 1052 and annular projection 1054. Shrink sleeve 1060 is provided to provide a leak proof seal. Clamping assembly 1000 is removable from a catheter assembly by removing each female luer adaptor 1050 from the clamping assembly 1000.

Figure 12:
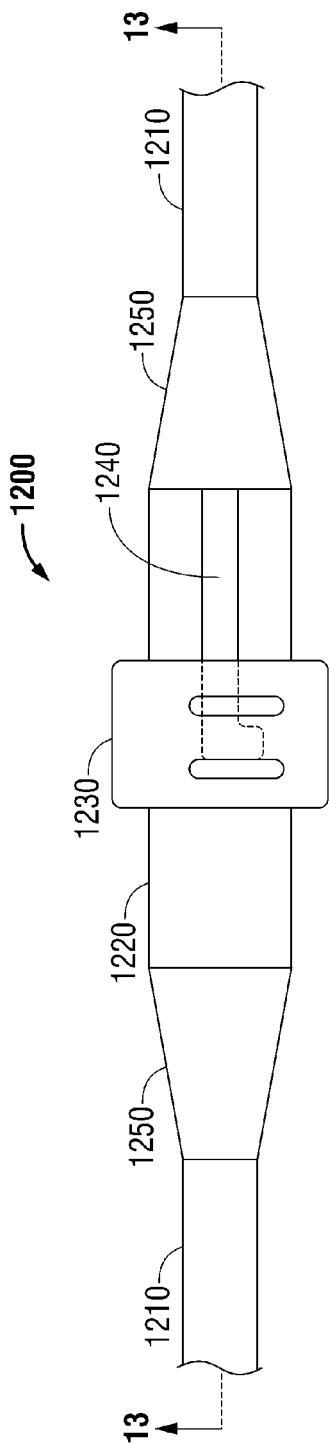
FIG. 12 is a side view of a catheter assembly with a clamping assembly according to another embodiment of the present disclosure.

FIG. 12 depicts a clamping assembly 1200 in accordance with another embodiment of the present disclosure. Clamping assembly 1200 is similar to clamping assembly 200 in that clamping assembly 1200 has a housing 1220, a deflecting member or slide tab 1230 and a track 1240. Distal end 1250 and proximal end 1260 of clamping assembly 1200 secure a conduit 1210 extending through the clamping assembly 1200. One end of conduit 1210 may be fluidly coupled or connected to a catheter and the other end of the conduit 1210 may be fluidly coupled or connected to a dialysis unit (not shown).

Figure 13:
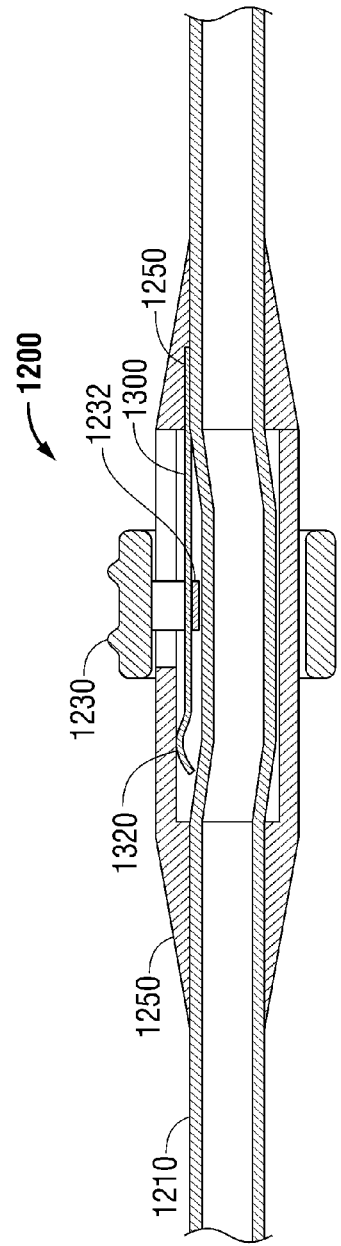
FIG. 13 is a cross-sectional view of the catheter assembly shown in FIG. 12 taken along the lines 13-13.

FIG. 13 depicts a cross section of the clamping assembly 1200 of FIG. 12 taken along the lines 13-13. As can be seen in FIG. 13, the clamping assembly 1200 has a conduit 1210 extending through the distal end 1250 and proximal end 1260 of the clamping assembly 1200. Adjacent to conduit 1210 is biasing element or metal spring member 1300 having a distal curved end 1320. Proximal end 1310 of biasing element 1300 is bonded or formed in proximal end 1260. Biasing element 1300 rests in cradle 1232 which is attached to slide tab 1230. Clamping assembly 1200 is movable relative to conduit 1210.

It will be understood that various modifications may be made to the embodiments of the presently disclosed clamping assemblies. For instance, the presently disclosed clamping assemblies may clamp any conduit capable of transferring fluid from one point to another. Therefore, the above description should not be construed as limiting, but merely as exemplifications of embodiments. Those skilled in the art will envision other modifications within the scope and spirit of the present disclosure.

What is claimed is:

1. A medical clamping assembly comprising:
   a housing defining a chamber;
   a deflecting member operable to slide relative to the housing between a first position and a second position;
   a conduit within the housing and being adapted for fluid coupling to a medical device; and
   a biasing element disposed within the housing adjacent to the conduit;
   the deflecting member being movable relative to the housing between the first position corresponding to an open state of the conduit and the second position corresponding to a closed state of the conduit whereby the biasing element compresses the conduit to substantially close a lumen of the conduit in the second position, wherein the deflecting member is normally biased toward the second position of the housing.

2. The medical clamping assembly according to claim 1, wherein the housing further comprises a track having at least one notch at the first position of the housing.

3. The medical clamping assembly according to claim 2, wherein the deflecting member slides in the track and held in place at the first position of the housing by the at least one notch.

4. The medical clamping assembly according to claim 1, wherein the biasing element is a metal spring member.

5. The medical clamping assembly according to claim 4, wherein the metal spring member is formed from stainless steel having a grade 301, 302, or 304.

6. The medical clamping assembly according to claim 4, wherein the metal spring is formed from a shape memory alloy.

7. The medical clamping assembly according to claim 6, wherein the shape memory alloy is nitinol.

8. The medical clamping assembly according to claim 1 further comprising a cradle coupled to the deflecting member and the biasing element rests on the cradle so that when the deflecting member is at the first position of the housing, the cradle prevents the biasing element from compressing the conduit.

9. The medical clamping assembly according to claim 8, wherein the biasing element is in a normally closed state and biases the deflecting member toward the second position of the housing.

10. The medical clamping assembly according to claim 1 further comprising an adaptor at a distal end of the housing, the adaptor is operatively connected to the medical device.

11. The medical clamping assembly according to claim 10, wherein the adaptor includes a luer connector.

12. The medical clamping assembly according to claim 1 further comprising an adaptor at a proximal end of the housing, wherein the adaptor secures the biasing element in the housing and is operatively connected to an extension conduit fluidly coupled to second medical device.

13. The medical clamping assembly according to claim 12, wherein the adaptor includes a luer connector.

14. The medical clamping assembly according to claim 1, wherein the medical device is a catheter.

15. The medical clamping assembly according to claim 12, wherein the second medical device is a dialysis unit.

16. A medical clamping assembly comprising:
    a housing defining a chamber;
    a deflecting member operable to slide along the housing between a first position and a second position; and
    a biasing element disposed within the housing adjacent to a conduit extending through the chamber of the housing;
    the deflecting member being movable relative to the housing between the first position corresponding to an open state and the second position corresponding to a closed position whereby the biasing element compresses the conduit to substantially close a lumen of the conduit in the second position, wherein the deflecting member is normally biased toward the second position of the housing.

17. The medical clamping assembly according to claim 16, wherein a first end of the conduit is fluidly coupled to a catheter and a second end of the conduit is fluidly coupled to a dialysis unit, the medical clamping assembly being movable relative to the conduit.

18. A catheter assembly, comprising:
    a catheter;
    a dialysis conduit; and
    a clamping assembly operatively connected in between the catheter and the dialysis conduit, the clamping assembly comprising a housing defining a chamber, a deflecting member operable to slide along the housing between a first position and a second position, a conduit extending through the housing and being adapted for fluid coupling to the catheter and the dialysis conduit, and a biasing element disposed within the housing adjacent to the conduit and coupled to the deflecting member, the deflecting member being movable relative to the housing between the first position corresponding to an open state of the conduit and the second position corresponding to a closed position of the conduit whereby the biasing element compresses the conduit to substantially close a lumen of the conduit in the second position, wherein the deflecting member is normally biased toward the second position of the housing.

* * * * *